United States Patent [19]
Sato et al.

[11] Patent Number: 4,746,668
[45] Date of Patent: May 24, 1988

[54] METHOD FOR TREATING RETINOPATHY

[75] Inventors: Takao Sato; Shinichiro Ashida; Kyoko Sakuma, all of Tokyo, Japan

[73] Assignee: Daiichi Seiyaku Co., Ltd., Tokyo, Japan

[21] Appl. No.: 896,366

[22] Filed: Aug. 14, 1986

[51] Int. Cl.$^4$ ............................................. A61K 31/44
[52] U.S. Cl. .................................... 514/341; 514/912
[58] Field of Search ...................... 514/402, 912, 341

[56] References Cited
U.S. PATENT DOCUMENTS 4,138,491  2/1979  Ishikawa et al. ................... 514/402

OTHER PUBLICATIONS

General Ophtholmology: 8$^{th}$ Ed. (1977) pp. 119-12-1-Lange Medical Publications; Los Altos, Calif.
Chem. Abst. 72:31790y (1970)-Walter.
Chem. Abst. 89:676n (1978)-Kosasagama et al.
Chem. Abst. 89:24299t (1978)-Ishikawa et al.
Chem. Abst. 96:136.449t (1982)-Rameda et al.
European J. Clin. Invest., 13, 231, 1983.
Doumyaku Kouka 12,1,139–143, (1984), Summary.

*Primary Examiner*—Douglas W. Robinson
*Attorney, Agent, or Firm*—Sughrue, Mion, Zinn, Macpeak & Seas

[57] ABSTRACT

A method for treating and preventing retinopathy which comprises administering a therapeutically effective amount of 2-(2-phenyl-2-(2-pyridyl))ethyl-2-imidazoline or a pharmaceutically acceptable salt thereof to a patient having retinopathy is disclosed.

4 Claims, No Drawings

METHOD FOR TREATING RETINOPATHY

FIELD OF THE INVENTION

This invention relates to a method for treating and preventing retinopathy.

BACKGROUND OF THE INVENTION

Diabetes is supposed to be one of the causes of retinopathy. At present, some antidiabetics which reduce the blood glucose level are used clinically; however, none of them is effective as treating agents for retinopathy. Therefore, it is thought that there is no correlation between the reduction in the blood glucose level and the treatment and prevention of retinopathy.

As the causes of retinopathy, impediment of blood stream in retinal vessels is suggested, as reported in Eur. J. clin. Invest., 13, 231, 1983. This impediment is supposed to be caused by aggregation of blood, and hence, inhibition of whole blood aggregation is supposed to have some correlation with the treatment and prevention of retinopathy.

It is known that 2-(2-phenyl-2-(2-pyridyl))ethyl-2-imidazoline reduces the blood glucose level and inhibits platelet aggregation and is useful as a antidiabetic agent, as disclosed in U.S. Pat. No. 4,138,491. However, as is apparent from the above description, the former activity of this compound does not suggest the application of this compound to the treatment and prevention of retinopathy.

Also, the latter activity of this compound does not suggest the application of this compound to the treatment and prevention of retinopathy. This is apparent from literature reference (Doumyaku Kouka 12, 1, 139–143, (1984)) which discloses that sensitivity of platelet aggregation in diabetic patients is the same as that in normal persons. However, this literature reference discloses that sensitivity of whole blood aggregation in diabetic patients is higher than that in normal persons.

Investigation had been made to find out the compound which inhibits the whole blood aggregation, and the present inventors found that the above-described compound has the activity for inhibiting the whole blood aggregation. Moreover, it was confirmed by clinical trial that the above compound was clinically useful for the treatment and prevention of retinopathy.

SUMMARY OF THE INVENTION

This invention relates to a method for treating and preventing retinopathy which comprises administering a therapeutically effective amount of 2-(2-phenyl-2-(2-pyridyl))ethyl-2-imidazoline (hereinafter, "Compound A") or a pharmaceutically acceptable salt thereof to a patient having retinopathy.

DETAILED DESCRIPTION OF THE INVENTION

This invention relates to a method for treating and preventing retinopathy which comprises a therapeutically effective amount of Compound A or the pharmaceutically acceptable salt thereof to a patient having retinopathy.

Examples of the pharmaceutically acceptable salts of Compound A include an acid addition salt with an inorganic acid such as hydrochloric acid, hydrobromic acid etc., and an organic acid such as maleic acid, fumaric acid, etc.

Compound A or the salt thereof inhibits strongly whole blood aggregation and is effective for the treatment and prevention of retinopathy. Accordingly, Compound A or the salt thereof is useful as a therapeutic and preventive agent in the treatment of retinopathy.

Compound A exhibits very low toxicity, and the acute toxicity ($LD_{50}$) of Compound A in rats has been found to be 867 mg/kg when administered orally.

For treating and preventing retinopathy, Compound A or the salt thereof can be administered orally 2 or 3 times daily at a dosage level of 150 to 1,500 mg/day, preferably, 300 to 900 mg/day in adult human.

Examples of the pharmaceutical preparations containing Compound A or the salt thereof include tablets, capsules, powders, granules and the like. These preparations can be prepared by conventional techniques using suitable additives such as binders, excipients, disintegrators and the like.

An example of the preparation containing the salt of Compound A is described below.

| Tablets | |
|---|---|
| Dihydrochloride sesquihydrate of Compound A | 100 mg |
| Lactose | 61 mg |
| Corn Starch | 32 mg |
| Hydroxypropyl Methylcellulose | 6 mg |
| Magnesium Stearate | 1 mg |
| Total | 200 mg |
| | per one tablet |

The present invention is further illustrated by the following examples, but the present invention is not limited thereto.

EXAMPLE 1

1. Materials (1) Blood

Blood was taken from median cubital vein or cephalic vein of normal men aged of 29 to 40, who had taken no anti-inflammatory drug at least for the last 10 days before testing, into a syringe containing 0.1 volume of 40 U/ml heparin aqueous solution (a product of Green Cross Corp., Japan).

(2) Preparation of neutrophil suspension 10 ml of the blood obtained above was mixed with 3 ml of a 4.5% dextran aqueous solution, and the mixture was allowed to stand for 1 hour at room temperature. The supernatant was taken and centrifuged at 250 X g for 7 minutes. The precipitate was taken, and 3 ml of 0.2% sodium chloride aqueous solution was added thereto to lyse the red blood cells. The mixture was allowed to stand for 75 seconds and 7 ml of a 1.2% sodium chloride aqueous solution was added thereto. The mixture was centrifuged at 250 X g for 7 minutes to obtain the precipitate which contained mainly neutrophils. When the red blood cell was not sufficiently removed, the above procedure for lysis of red blood cell was repeated. The precipitate was washed with 10 ml of a phosphate buffer solution containing 0.5% glucose (hereinafter, PBSG), and the mixture was centrifuged at 250 X g for 7 minutes to take the precipitate. The above washing procedure was repeated twice, and the precipitate obtained was added to PBSG or PBSG containing 0.5% human serum albumin to obtain the neutrophil suspension. It was confirmed that the surviving ratio of nuetrophil in the resulting suspension was over 95% as determined by the trypan blue staining method. A blood cell counter (a product of Nihon Koden Co., Ltd) was used to count the number of neutrophils. The mixture was preserved at 4° C. before use.

(3) Preparation of platelets rich plasma

The blood obtained in (1) was centrifuged at 190 X g for 7 minutes. The supernatant was taken to obtain the platelets rich plasma (hereinafter, PRP). Platelet counter (a product of Toa Co., Ltd) was used to count the number of platelets.

(4) Reagent

Compound A was dissolved in a saline, and the solution obtained was used in the experiment.

As an aggregation inducing agent, an aqueous solution prepared by dissolving epinephrine or a platelet activating factor (hereinafter, PAF) in 25 mM Tris HCl-130 mM NaCl aqueous solution (pH 7.4) was used in the experiment.

2. Determination of whole blood aggregation (1) Impedance method

5 µl of saline solution of Compound A prepared in 1-4 was added to 1 ml of the whole blood, neutrophil suspension or PRP and an electrode was dipped thereinto. The mixture obtained was incubated for 2 minutes under the conditions that the temperature in cell was 37° C. and the stirring rate was 1000 r.p.m., and then 20 µl of aggregation inducing agent was added to the mixture. 4 minutes later, the variation in impedance ($\Delta\Omega$) was determined using Chrono-log aggregometer (540 type, a product of Chrono-log Co., Ltd). The intensity of the variation gave the aggregation activity. In determining the aggregation of neutrophils, 5 µg/ml of cytochalasin B was added to the incubated mixture, one minute prior to the addition of PAF solution. As a control, saline was used instead of saline solution of Compound A and the aggregation was determined as described above.

(2) Optical method

5 µl of saline solution of Compound A prepared in 1-4) was added to 1 ml of neutrophil suspension and the mixture was incubated for 2 minutes under the conditions that the temperature in cell was 37° C. and the stirring rate was 1,000 r.p.m. 20 µl of PAF solution was added to the preincubated mixture to induce the aggregation of neutrophils. 1 minute prior to the addition of PAF solution, 5 µg/ml of cytochalasin B was added to the mixture. The aggregation was determined optically using the Chrono-log aggregometer. As a control, saline was used instead of saline solution of Compound A and the aggregation was determined as described above.

3. Result

The results are shown in the following tables.

(1) Inhibition by the compound A of human whole blood aggregation

TABLE 1

|  | $IC_{50}$ (µM, in vitro) | |
| --- | --- | --- |
|  | Epinephrine (2 µM) | PAF (0.02 µM) |
| (n = 3) | 5.6 | 1.8 |
|  | 4.2 | 4.6 |
|  | 5.8 | 2.8 |
| average ± s.d. | 5.2 ± 0.7 | 2.8 ± 1.2 |

As is apparent from the above table, Compound A inhibited the human whole blood aggregation induced by epinephrine (2 µM) with the $IC_{50}$ of about 5 µM (n=3). Also, Compound A inhibited strongly the human whole blood aggregation induced by PAF (0.02 µM). The $IC_{50}$ data were in the range of 0.85 to 4.6 µM and the average thereof was 2.8 µM (n=3). Therefore, it was confirmed that Compound A inhibited the whole blood aggregation at a low concentration.

(2) Inhibition by Compound A of neutrophil aggregation (a) Inhibition by Compound A of PAF-induced adhesion-aggregation of human neutrophils (Impedance method)

TABLE 2

| Concentration of Compound A (µM) | Inhibition ratio (%) | |
| --- | --- | --- |
| 10 | 59 | (PAF, 0.02 µM) |

(b) Inhibition by Compound A of PAF-induced human neutrophil aggregation (Optical method)

TABLE 3

| Concentration of Compound A (µM) | inhibition ratio (%) | |
| --- | --- | --- |
| 5 | 68 | (PAF, 2 µM) |
| 10 | 83 | |

(c) Inhibition by Compound A of PAF-induced human platelet aggregation.

TABLE 4

| Concentration of Compound A (µM) | Inhibition ratio (%) | |
| --- | --- | --- |
| 10 | 0 | (PAF, 2 µM) |
| 50 | 45 | |
| 100 | 82 | |

As is apparent from the above tables, Compound A inhibited the PAF-induced human neutrophil aggregation at low concentration. However, Compound A did not inhibit PAF-induced human platelet aggregation at a low concentration but did at a high concentration. These results suggest that the inhibition of whole blood aggregation by Compound A correlated to the inhibition of neutrophil aggregation.

When PAF is injected into retinal artery of rabbit, a sludge-like state is observed in retinal vesseles. Since this sludge-like state is also observed in thrombocytopenia, it is supposed that this sludge-like state is not caused by the platelet aggregation but is caused by the neutrophil aggregation (Platelet-activating factor INSERN Symposium No. 23 PP223-230, 1983). This sludge-like state is similar to those observed in human retinopathy (Advances in Microcirculation: the microcirculation diabetics, 18, PP1-11, 1979). In a patient having diabetic retinopathy, it is supposed that the production of PAF is accelerated by activation of platelet functions (Eur. J. clin. Invest., 13, 231, 1983). Accordingly, PAF-induced neutrophil aggregation, that is, whole blood aggregation is supposed to be strongly involved in occurrence and progress of retinopathy.

The compound A inhibited human whole blood aggregation and human neutrophil aggregation induced by PAF. Thus Compound A is useful as an agent for treatment and prevention of retinopathy.

EXAMPLE 2 (Clinical Trial)

Compound A was administered orally at dose of 300 to 900 mg daily to patients having diabetic retinopathy for a period of a month to about 2 years. Microaneurysms, dot hemorrhage, retina edema, hard exudate, arterialization and maculopathy in *Fundus oculi*, which were indications for retinopathy, were investigated using a funduscope. The results were shown in the following Table 5.

TABLE 5

| Patient | Indication | Funduscopic obserbation | | | | | |
|---------|------------|---|---|---|---|---|---|
| | | 75 days prior to administration | | at start of administration | | 58 weeks after administration | |
| A | microaneurysms | − | − | + | + | − | − |
| | | 28 days prior to administration | | at start of administration | | 116 weeks after administration | |
| B | microaneurysms | + | + | + | + | − | − |
| | dot hemorrhage | + | + | + | + | − | − |
| | | 44 days prior to administration | | at start of administration | | 109 weeks after administration | |
| C | dot hemorrhage | + | + | + | + | ± | ± |

+: observed
±: slightly observed
−: not observed
*In the column of funduscopic observation, the left indication means the observation in left eye and the right one means that in right eye.
**In the above patients, indications other than those shown in the table were not observed.

As is apparent from Table 5, disappearance or reduction of microaneurysms and dot hemorrhage were observed in those 3 patients by administration of Compound A.

Accordingly, it was clinically confirmed that Compound A is useful as a treating and preventing agent for retinopathy.

What is claimed is:

1. A method for treating diabetic retinopathy which comprises administering a therapeutically effective amount of 2-(2-phenyl-2-(2-pyridyl))ethyl-2-imidazoline or a pharmaceutically acceptable salt thereof to a patient having retinopathy.

2. A method as claimed in claim 1, wherein the therapeutically effective amount is in the range of 150 to 1500 mg/day by oral administration.

3. A method as claimed in claim 1, wherein 2-(2-phenyl-2-(2-pyridyl))ethyl-2-imidazoline or the pharmaceutically acceptable salt thereof is administered orally in the form of tablets.

4. A method as claimed in claim 1, wherein 2-(2-phenyl-2-(2-pyridyl))ethyl-2-imidazoline or the pharmaceutically acceptable salt thereof is administered orally in the form of powders.

* * * * *